(12) United States Patent
Ikeda et al.

(10) Patent No.: US 6,194,461 B1
(45) Date of Patent: Feb. 27, 2001

(54) NITRONE DERIVATIVES

(75) Inventors: Kazuhito Ikeda; Tohru Tatsuno, both of Hyogo; Hiroki Ogo, Kanagawa; Shuji Masumoto, Osaka; Tatsuya Fujibayashi; Ryu Nagata, both of Hyogo, all of (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/254,856
(22) PCT Filed: Sep. 22, 1997
(86) PCT No.: PCT/JP97/03377
§ 371 Date: Mar. 15, 1999
§ 102(e) Date: Mar. 15, 1999
(87) PCT Pub. No.: WO98/13332
PCT Pub. Date: Apr. 2, 1998

(30) Foreign Application Priority Data

Sep. 26, 1996 (JP) .................................................... 8-277545

(51) Int. Cl.$^7$ ........................ A61K 31/15; C07C 251/00; C07C 251/32
(52) U.S. Cl. .......................... 514/579; 514/640; 514/645; 564/265; 564/300
(58) Field of Search .................................... 564/253, 297, 564/265, 300; 514/640, 644, 579, 645

(56) References Cited

U.S. PATENT DOCUMENTS

| | | | |
|---|---|---|---|
| Re. 36,594 | * | 2/2000 | Janzen et al. ......................... 514/579 |
| 6,051,571 | * | 4/2000 | Kelleher et al. ................... 514/231.5 |
| 6,083,988 | * | 7/2000 | Becker ................................. 514/640 |
| 6,083,989 | * | 7/2000 | Flitter et al. ......................... 514/460 |

FOREIGN PATENT DOCUMENTS

| | | |
|---|---|---|
| 44-23322 | 10/1969 | (JP) . |
| 49-135962 | 12/1974 | (JP) . |
| 9-278652 | 10/1997 | (JP) . |
| 91 05552 | 5/1991 | (WO) . |
| 9222290 | 12/1992 | (WO) . |
| 9517876 | 7/1995 | (WO) . |

OTHER PUBLICATIONS

N. Nakao et al, Neuroscience, 73(1) (1996) p. 185–200.
Tahereh Tabatabie et al, Biochem. Biophys. Res. Commun., 221 (1996) p. 386–390.
D.W. Newell, et al, J. Neuroscience, 15 (11) (1995) p. 7702–7711.
J.B. Schultz et al, Neuroscience, 71 (4) (1996) p. 1043–1048.
A.M. van der Hagen et al, J. Am. Optometric Assoc., 64 (12) (1993) p. 871–878.
Samy B. Said et al, Liebigs. Ann. Chem., (5) (1990) p. 461–464, p. 461, right column, 4e.
Chem. Abstr., vol. 55 (1961) the abstract No. 23559i.
Craig E. Thomas et al., Journal of Biol. Chem., 271(6) (1996) p. 3097–3104.
Kenneth T. Brown, Vision Res. vol. 8, pp. 633–677. (Received Dec. 18, 1967).
Castagne et al., Proc. R. Soc. B. Biol. Sci., 1996, 263 (1374):1193–7.

* cited by examiner

*Primary Examiner*—Deborah C. Lambkin
(74) *Attorney, Agent, or Firm*—Birch, Stewart, Kolasch & Birch, LLP

(57) ABSTRACT

A compound represented by the figure (1) or a pharmaceutically acceptable salt thereof is useful as medicament for treating retinal degenerative disorders:

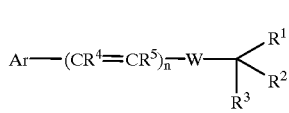

(1)

wherein Ar is optionally substitued phenyl or optionally substituted heteroaryl;.

n is 0, 1 or 2;

W is —$CH_2NH$— or —$CH=N(O)$—;

$R^1$, $R^2$ and $R^3$ are independently optionally substituted alkyl, carboxyl or alkoxycarbonyl; any two groups of $R^1$, $R^2$ and $R^3$ may be taken together with the carbon atom to form optionally substituted cycloalkane; all of $R^1$, $R^2$ and $R^3$ may be taken together with the adjusent carbon atom to form optionally substituted bicycloalkane or optionally substituted tricycloalkane;

$R^4$ and $R^5$ are independently hydrogen atom or optionally substituted alkyl.

14 Claims, No Drawings

NITRONE DERIVATIVES

This application is the national phase under 35 U.S.C. §371 of prior PCT International Application No. PCT/JP97/03377 which has an International filing date of Sep. 22, 1997 which designated the United States of America.

TECHNICAL FIELD

The present invention relates to a nitrone derivative and a precursor thereof useful as a medicament. The nitrone derivative and a precursor thereof are useful as a medicament for treating neurodegenerative disorders such as retinal degenerative disorders and the like.

BACKGROUND ART

The nitrone derivatives such as phenyl-t-butylnitrone (PBN) have been used as spin-traps to detect free radicals by electron spin resonance (ESR). J. Org. Chem., 57, 2624 (1992) describes the syntheses of various mono-substituted PBN derivatives and their effects as spin traps.

It has been reported that the nitrone derivatives such as PBN would be useful as medicaments for treating the diseases caused by active oxygen damages (e.g. ischemia, infection, inflammation, radiation damages, damages of central or peripheral nervous systems or peripheral organs caused by drug abuse, etc.) by acting as antioxidants (WO 91/5552; WO 92/22290; WO 95/17876; J. Biol. Chem., 271, 3097(1996)). However, these documents do not disclose that these compounds are effective for treating retinal degenerative disorders. It is also reported that free radicals such as active oxygen have some relation with retinal damages caused by light (A. M. Van Der Hagen, et al., J. Am. Optom. Assoc., 64, 871(1993)).

JP 54-2324 (A) discloses the syntheses of compounds useful as insecticides using N-t-butyl-4-chlorobenzylamine, N-t-butyl-2,4-dichlorobenzylamine and the like as synthetic intermediates.

DESCRIPTION OF THE INVENTION

The present invention is intended to provide a novel compound useful as a medicament for treating neurodegenerative disorders (e.g. neurodegenerative disorders induced by stroke, hypoglycemia, cardiac arrest, perinatal apparent death and the like; epilepsy; Huntington's chorea; Alzheimer's disease; diabetic neuropathy; retinal degenerative disorders and the like).

The present invention is also intended to provide a medicament for treating retinal degenerative disorders (e.g. retinitis pigmentosa, senile macular degeneration, diabetic retinopathy, glaucoma, traumatic retinodialysis, etc.)

The inventors of the present invention have intensively carried out research, and found that nitrone derivatives are useful as a medicament for treating neurodegenerative disorders such as retinal degenerative disorders and the like, and that the corresponding amine which would be converted to the nitrone derivative in human bodies, have similar effects. Thus, the present invention has been accomplished.

The present inventions are as follows:

[1] A medicament for treating retinal degenerative disorder comprising a compound represented by the figure 1 or a pharmaceutically acceptable salt thereof:

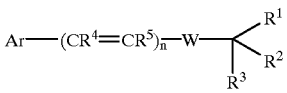

(1)

wherein Ar is optionally substituted phenyl or optionally substituted heteroaryl;
n is 0, 1 or 2;
W is —CH$_2$NH— or —CH=N(O)—;
R$^1$, R$^2$ and R$^3$ are independently optionally substituted alkyl, carboxyl or alkoxycarbonyl; any two groups of R$^1$, R$^2$ and R$^3$ may be taken together with the carbon atom to form optionally substituted cycloalkane; all of R$^1$, R$^2$ and R$^3$ may be taken together with the adjacent carbon atom to form optionally substituted bicycloalkane or optionally substituted tricycloalkane;
R$^4$ and R$^5$ are independently hydrogen atom or optionally substituted alkyl, and

[2] A compound represented by the figure 2 or a pharmaceutically acceptable salt thereof:

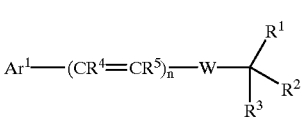

(2)

wherein n, W, R$^1$, R$^2$, R$^3$, R$^4$ and R$^5$ are as defined above;
Ar$^1$ is optionally substituted 5-membered heteroaryl or a group represented by the Figure 3:

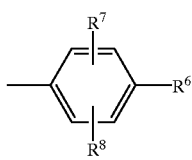

wherein R$^6$ is halogen atom, trifluoromethyl, cyano or nitro;
R$^7$ is hydrogen atom or a substitutent;
R$^8$ is a substituent;
provided that Ar$^1$ is not dichlorophenyl when W is —CH$_2$NH—.

Heteroaryl includes, for example, 5- or 6-membered heteroaryl containing 1 to 3 atoms selected independently from nitrogen atoms, sulfur atoms and oxygen atoms, and the like. 5-Membered heteroaryl includes, for example, 5-membered heteroaryl containing 1 to 3 atoms selected independently from nitrogen atoms, sulfur atoms and oxygen atoms, and the like. Typical examples are 5-membered heteroaryl containing 1 or 2 atoms selected independently from nitrogen atoms, sulfur atoms and oxygen atoms such as pyrrolyl, thienyl, furyl, imidazolyl, pyrazolyl, isothiazolyl, isoxazolyl, and the like. 6-Membered heteroaryl includes, for example, 6-membered heteroaryl containing 1 to 3 nitrogen atoms, and the like. Typical examples are pyridyl, pyrazinyl, pyrimidinyl, pyridazinyl, triazinyl, and the like.

Heterocyclic group includes heteroaryl, heterocycloalkyl and the like. Heterocycloalkyl includes, for example, 5- or 6-membered heterocycloalkyl containing 1 to 3 atoms selected independently from nitrogen atoms, sulfur atoms and oxygen atoms, and the like. 5-Membered heterocycloalkyl includes, for example, 5-membered heterocycloalkyl containing 1 to 3 atoms selected independently from nitrogen atoms, sulfur atoms and oxygen atoms, and the like. Typical example is 5-membered heterocycloalkyl containing 1 or 2 atoms selected independently from nitrogen atoms, sulfur atoms and oxygen atoms, such as pyrrolidinyl, pyrrolinyl, imidazolidinyl, pyrazolidinyl, tetrahydrofuryl, tetrahydrothienyl, dioxolanyl and the like. 6-Membered heterocycloalkyl includes, for example, 6-membered heterocycloalkyl containing 1 to 3 atoms selected independently from nitrogen atoms, sulfur atoms and oxygen atoms, and the like. Typical example is 6-membered heterocycloalkyl containing 1 or 2 atoms selected independently from nitrogen atoms, sulfur atoms and oxygen atoms, such as piperidyl, piperazinyl, morpholinyl, tetrahydropyranyl, dioxanyl and the like.

The substituent of substituted phenyl and substituted heteroaryl includes, for example, halogen atom, cyano, nitro, alkyl, alkyl substituted by halogen atom(s), alkoxy, alkoxycarbonyl, carbamoyl, carbamoyl substituted by alkyl (s) and the like. Phenyl and heteroaryl may be substituted independently by one or more substituents. Typical examples are the electron-withdrawing groups such as halogen atom, cyano, nitro, trifluoromethyl and the like. Preferable is halogen atom, and most preferable is fluorine atom.

The number of substituents of substituted aryl may be 1, 2 or 3. Typical examples are 1 and 2, and preferable is 2. Typical positions of the substitution are 4th position and 2nd and 4th positions if the aryl is substituted by 2 substituents.

Alkyl includes straight or branched $C_1$–$C_6$ alkyl. Typical examples are methyl, ethyl, propyl, 1-methylethyl, butyl, 2-methylpropyl, pentyl, 1,2-dimethylpropyl, hexyl, 3-ethylbutyl and the like.

Alkoxy includes straight or branched $C_1$–$C_6$ alkoxy. Typical examples are methoxy, ethoxy, propoxy, 1-methylethoxy, butoxy, 2-methylpropoxy, pentyloxy, 1,2-dimethylpropoxy, hexyloxy, 3-ethylbutoxy and the like.

Alkoxyalkoxy is the alkoxy substituted by alkoxy.

Alkoxycarbonyl is the carbonyl substituted by alkoxy.

Halogen-substituted alkyl and halogen-substituted alkoxy are the alkyl and alkoxy substituted by one halogen atom or more. Typical examples are trifluoromethyl, trifluoromethoxy and the like.

Alkanoyl of alkanoyloxy and alkanoylamino includes, for example, straight or branched $C_1$–$C_6$ alkanoyl. Typical examples are formyl, acetyl, propionyl, butyryl, isobutyryl, valeryl, isovaleryl, pivaloyl, 2-methylbutyryl, hexanoyl and the like.

Cycloalkyl includes, for example, $C_3$–$C_8$ cycloalkyl. Typical examples are cyclopropyl, cyclobutyl, cyclopentyl, cyclohexyl, cycloheptyl, cyclooctyl and the like.

In the carbamoyl substituted by alkyl(s), the carbamoyl may be substituted independently by 1 or 2 alkyl(s).

Halogen atom includes, for example, fluorine atom, chlorine atom, bromine atom, iodine atom and the like. Typical examples are fluorine atom, chlorine atom and bromine atom, and preferable is fluorine atom.

Cycloalkane includes, for example, $C_3$–$C_8$ cycloalkane. Typical examples are cyclopropane, cyclobutane, cyclopentane, cyclohexane, cycloheptane, cyclooctane and the like.

Bicycloalkane includes, for example, $C_7$–$C_{10}$ bicycloalkane. Typical examples are bicyclo[2.2.1]heptane, bicyclo[2.2.2]octane and the like.

Tricycloalkane includes, for example, $C_7$–$C_{13}$ tricycloalkane. Typical examples are adamantane and the like.

The substituent of substituted alkyl, substituted cycloalkane, substituted bicycloalkane and substituted tricycloalkane includes, for example, cycloalkyl, heterocyclic group, alkoxy, alkoxyalkoxy, alkanoyloxy, alkanoylamino and the like. Alkyl, cycloalkane, bicycloalkane and tricycloalkane may be substituted independently by one or more substituents.

Typical examples of Ar as used in Figure 1 and $Ar^1$ as used in figure 2 are 2-thienyl and the group represented by Figure 3:

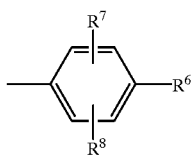

wherein $R^6$, $R^7$ and $R^8$ are as defined above.

Preferable are 2-thienyl and the group represented by figure 4:

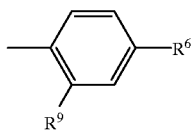

wherein $R^6$ is as defined above;

$R^9$ is halogen atom, cyano, nitro, alkyl, alkyl substituted by halogen atom(s), alkoxy, alkoxycarbonyl, carbamoyl or carbamoyl substituted by alkyl(s).

More preferable are 2-thienyl and phenyl substituted by 2 halogen atoms at 2nd and 4th positions.

Typical example of $R^1$, $R^2$ and $R^3$ as used in figure 1 and 2 is optionally substituted alkyl, and preferable is methyl.

Typical example of W as used in figure 1 and 2 is —CH=N(O)—.

Typical examples of n as used in figure 1 and 2 are 0 and 1, and preferable is 0.

The pharmaceutically acceptable salts include, for example, salts with inorganic acids and salts with organic acids. Salts with inorganic acids includes, for example, hydrochloride, hydrobromide, iodide, sulfate and the like. Salts with organic acids include, for example, acetate, oxalate, citrate, malate, tartrate, maleate, fumarate and the like. The compounds represented by figure 1 or 2 and the pharmaceutically acceptable salts thereof include their solvates such as the hydrate and the like. The compounds represented by figure 1 or 2 include their tautomers if the tautomers exist. The compounds represented by figure 1 or 2 include the mixture of their geometrical isomers and the isolated isomer if the geometrical isomers exist.

The compound of figure 1 or 2 can be produced for example by the following methods. In the following, the compound of figure 1 is used as a representative and the methods are described separately in the case that W is —CH$_2$NH— and in the case that W is —CH=N(O)—.

I. The case that W is —CH$_2$NH—.

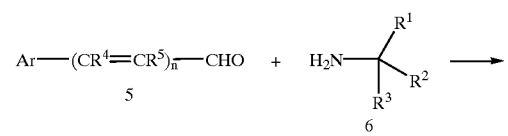

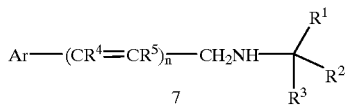

wherein Ar, n, $R^1$, $R^2$, $R^3$, $R^4$ and $R^5$ are as defined above.

The compound of figure 7 of the present invention can be produced by performing reductive amination reaction between the aldehyde of figure 5 and the amine of figure 6 in a suitable solvent in the presence of a suitable reducing agent (J. Org. Chem., 55, 1736(1990)). In the reductive amination reaction, borohydride such as $NaBH_4$, $NaBH_3CN$ and the like may be used as a suitable reducing agent, and hydrogenation in the presence of a metal catalyst such as palladium and the like may be used. Alcohol such as methanol, ethanol and the like may be used as a suitable solvent. The reaction temperature may be in the range between 0° C. and room temperature. The compounds of figure 5 and 6 are commercially available or may be easily produced by conventional methods.

II The case that W is —CH=N(O)—.

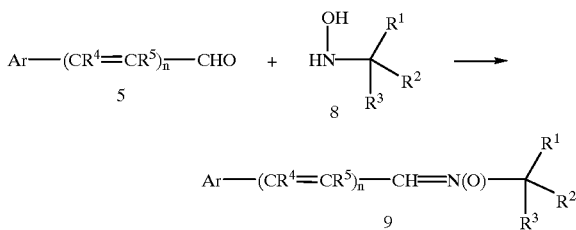

wherein Ar, n, $R^1$, $R^2$, $R^3$, $R^4$ and $R^5$ are as defined above.

The compound of figure 9 of the present invention can be produced by reacting the aldehyde of figure 5 and the hydroxylamine of figure 8 in a suitable solvent. Acid may be added if needed. Toluene, chloroform, ethyl acetate, THF, diethyl ether, methanol, ethanol and the like may be used as a suitable solvent. Protic acid such as p-toluenesulphonic acid, trichloroacetic acid, acetic acid and the like and Lewis acid such as phosphorus oxychloride, $BF_3$, $ZnCl_2$ and the like may be used as an acid. The reaction temperature may be in the range between room temperature and the boiling point of the solvent.

The compound of figure 8 may be easily produced by known methods (J. Org. Chem., 57, 2624(1992)). For example, N-hydroxy-t-butylamine can be produced by reducing 1,1-dimethylnitroethane with zinc in the presence of acetic acid. The compound of figure 8 may be produced and immediately used in the next reaction in the same vessel.

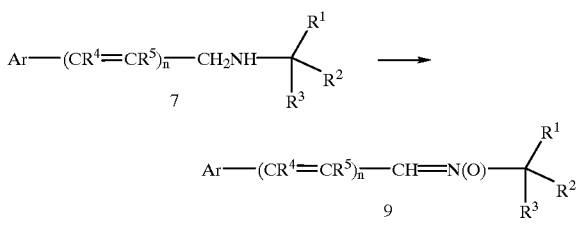

wherein Ar, n, $R^1$, $R^2$, $R^3$, $R^4$ and $R^5$ are as defined above.

The compound of figure 9 of the present invention can be obtained by oxidizing the compound of figure 7 with a suitable oxidizing agent (J. Org. Chem., 55, 1736(1990)). Oxidation reaction was performed by using an oxidizing agent such as hydrogen peroxide and the like with a catalyst such as $Na_2WO_4$ and the like. Organic solvent suitably includes, for example, alcohol such as methanol, ethanol and the like. Reaction temperature is usually in the range between 0° C. and the boiling point of the solvent, preferably at room temperature.

The compound of figure 1 or 2 can be purified by the conventional method. For example, the compound can be purified by column chromatography, recrystallization and the like. Recrystallization solvent includes, for example, alcohol such as methanol, ethanol, 2-propanol and the like; ether such as diethyl ether and the like; ester such as ethyl acetate and the like; aromatic solvent such as toluene and the like; ketone such as acetone and the like; hydrocarbon solvent such as hexane and the like; water and the like; and mixture thereof. Pharmaceutically acceptable salt of the compound of figure 1 or 2 can be formed by the conventional method, and the salt may be purified by recrystallization or the like.

The compound of figure 1 or 2 and the pharmaceutically acceptable salt thereof may be administered orally or parenterally. Pharmaceutical forms for oral administration include, for example, tablets, capsules, syrups, suspensions and the like. Pharmaceutical forms for injection include, for example, solution, emulsions, suspensions and the like. Suppository may be also applicable.

These compositions can be prepared by mixing the active compound with conventional carriers, excipients, binders, stabilizers and the like. Injection may contain buffers, solubilizers, agents for influencing osmotic pressure and the like.

The dose and the times for administration varies widely depending on the grade of the symptoms, the patient's age, body weight, administration route and the like. But the compound is usually administered to an adult in a dose of approximately 1–1000 mg, preferably 10–500 mg once or several times per day, by the oral route. By injection, the compound is usually administered to an adult in a dose of approximately 0.1–500 mg, preferably 3–100 mg in once or several times per day.

EXAMPLES

The present invention will be described in detail below, referring to examples, which are not limitative of the present invention.

Example 1

Production of α-(2,4-difluorophenyl)-N-t-butylnitrone

To a suspension of 2,4-difluorobenzaldehyde (608.9 mg, 4.28 mmol), 1,1-dimethylnitroethane (881.9 mg, 8.55 mmol) and zinc (840.0 mg, 12.8 mmol) in ethanol (15 ml) was added acetic acid (1.54 g, 25.6 mmol) dropwise at 5° C. while stirring. The mixture was stirred at room temperature for one day. After the mixture was cooled to 5° C., zinc acetate was filtered off and the filtrate was concentrated and purified by silica gel chromatography (hexane/ethyl acetate= 4/1).

Yield: 852.5 mg(93%)

$^1$H-NMR(CDCl$_3$) 1.62(s, 9H), 6.80–6.88(m, 1H), 6.90–6.98(m, 1H), 7.79(s, 1H), 9.38–9.47(m, 1H)

Example 2

Production of α-(2,4-dichlorophenyl)-N-t-butylnitrone

To a suspension of 2,4-dichlorobenzaldehyde (462.1 mg, 2.64 mmol), 1,1-dimethylnitroethane (543.1 mg, 5.27 mmol) and zinc (514.8 mg, 7.88 mmol) in ethanol (3.0 ml) was added acetic acid (944.8 mg, 15.7 mmol) dropwise at 5° C. while stirring. The mixture was stirred at room temperature for one day. Zinc acetate was filtered off and the filtrate was concentrated and purified by silica gel chromatography (hexane/ethyl acetate=5/1).

Yield: 436.6 mg(67%)

$^1$-NMR(CDCl$_3$) 1.62(s, 9H), 7.30–7.34(m, 1H), 7.43(d, 1H, J=2.3 Hz), 8.04(s, 1H), 9.39(d, 1H, J=8.9 Hz)

Example 3

Production of α-(2-methoxyphenyl)-N-t-butylnitrone

To a suspension of 2-methoxybenzaldehyde (622.4 mg, 4.57 mmol), 1,1-dimethylnitroethane (942.7 mg, 9.14 mmol) and zinc (896.3 mg, 13.7 mmol) in ethanol (15 ml) was added acetic acid (944.8 mg, 15.7 mmol) dropwise at 5° C. while stirring. The mixture was stirred at room temperature for one day. After the mixture was cooled to 5° C., zinc acetate was filtered off and the filtrate was concentrated and purified by silica gel chromatography (hexane/ethyl acetate=2/1).

Yield: 877.2 mg(93%)

$^1$H-NMR(CDCl$_3$) 1.61(s, 9H), 3.87(s, 3H), 6.89(d, 1H, J=8.3 Hz), 7.02(t, 1H, J=7.9 Hz), 7.32–7.39(m, 1H), 8.05(s, 1H), 9.36(dd, 1H, J=1.7, 7.9 Hz)

Example 4

Production of α-(2-fluorophenyl)-N-t-butylnitrone

To a suspension of 2-fluorobenzaldehyde (332.3 mg, 2.68 mmol), 1,1-dimethylnitroethane (547.5 mg, 5.31 mmol) and zinc (514.6 mg, 7.87 mmol) in ethanol (3.0 ml) was added acetic acid (940.2 mg, 15.7 mmol) dropwise at 5° C. while stirring. The mixture was stirred at room temperature for 6.5 hours. Zinc acetate in the mixture was filtered off and the filtrate was concentrated and purified by silica gel chromatography (hexane/ethyl acetate=4/1 to 2/1).

Yield: 489.0 mg(93%)

$^1$H-NMR(CDCl$_3$) 1.63(s, 9H), 7.04–7.12(m, 1H), 7.18–7.24(m, 1H), 7.32–7.41(m, 1H), 7.87(s, 1H), 9.29–9.36(m, 1H)

Example 5

Production of α-(3-fluorophenyl)-N-t-butylnitrone

To a suspension of 3-fluorobenzaldehyde (327.5 mg, 2.64 mmol), 1,1-dimethylnitroethane (542.3 mg, 5.26 mmol) and zinc (517.9 mg, 7.92 mmol) in ethanol (3.0 ml) was added acetic acid (946.2 mg, 15.8 mmol) dropwise at 5° C. while stirring. The mixture was stirred at room temperature for 5 hours. Zinc acetate in the mixture was filtered off and the filtrate was concentrated and purified by silica gel chromatography (hexane/ethyl acetate=2/1).

Yield: 448.8 mg(87%)

$^1$H-NMR(CDCl$_3$) 1.62(s, 9H), 7.06–7.13(m, 1H), 7.32–7.41(m, 1H), 7.56(s, 1H), 7.77(d, 1H, J=7.9 Hz), 8.33–8.39(m, 1H)

Example 6

Production of α-(4-fluorophenyl)-N-t-butylnitrone

To a suspension of 4-fluorobenzaldehyde (325.0 mg, 2.62 mmol), 1,1-dimethylnitroethane (542.3 mg, 5.26 mmol) and zinc (516.0 mg, 7.89 mmol) in ethanol (3.0 ml) was added acetic acid (941.7 mg, 15.7 mmol) dropwise at 5° C. while stirring. The mixture was stirred at room temperature for 4.5 hours. Zinc acetate in the mixture was filtered off and the filtrate was concentrated and purified by silica gel chromatography (hexane/ethyl acetate=2/1–1/1).

Yield: 432.1 mg(84%)

$^1$H-NMR(CDCl$_3$) 1.61(s, 9H), 7.10(dd, 2H, J =8.7, 8.7 Hz), 7.53(s, 1H), 8.31–8.36(m, 2H)

Example 7

Production of α-(2,6-difluorophenyl)-N-t-butylnitrone

To a suspension of 2,6-difluorobenzaldehyde (374.7 mg, 2.64 mmol), 1,1-dimethylnitroethane (541.6 mg, 5.25 mmol) and zinc (517.0 mg, 7.91 mmol) in ethanol (3.0 ml) was added acetic acid (940.5 mg, 15.7 mmol) dropwise at 5° C. while stirring. The mixture was stirred at room temperature for 5 hours. Zinc acetate in the mixture was filtered off and the filtrate was concentrated and purified by silica gel chromatography (hexane/ethyl acetate=5/2–2/1).

Yield: 488.2 mg(87%)

$^1$H-NMR(CDCl$_3$) 1.64(s, 9H), 6.93(dd, 2H, J =8.2, 8.2 Hz), 7.27–7.38(m, 1H), 7.58(s, 1H)

Example 8

Production of α-(4-(1-imidazolyl)phenyl)-N-t-butylnitrone

To a suspension of 1,1-dimethylnitroethane (261.2 mg, 2.53 mmol) and zinc (247.0 mg, 3.78 mmol) in ethanol (3.0 ml) was added acetic acid (451.8 mg, 7.52 mmol) dropwise at 5° C. while stirring. The mixture was stirred at room temperature for 30 minutes. After cooling the mixture to 5° C. again, 4-(1-imidazolyl)benzaldehyde (216.5 mg, 1.26 mmol) was added dropwise to the mixture while stirring and stirred at room temperature overnight. Zinc acetate in the mixture was filtered off and the filtrate was concentrated and purified by silica gel chromatography (chloroform/methanol=10/1).

Yield: 126.5 mg(41%)

$^1$H-NMR(CDCl$_3$) 1.64(s, 9H), 7.22(d, 1H, J =1.0 Hz), 7.34(s, 1H), 7.45(d, 2H, J =8.7 Hz), 7.61(s, 1H), 7.93(s, 1H), 8.44(d, 2H, J=8.7 Hz)

Example 9

Production of α-(2-pyridyl)-N-t-butylnitrone

To a suspension of 1,1-dimethylnitroethane (545.5 mg, 5.29 mmol) and zinc (516.6 mg, 7.90 mmol) in ethanol (3.0 ml) was added acetic acid (950.1 mg, 15.8 mmol) dropwise at 5° C. while stirring. The mixture was stirred at room temperature for 20 minutes. After cooling the mixture to 5° C. again, 2-pyridinecarbaldehyde (283.9 mg, 2.65 mmol) was added dropwise to the mixture while stirring and stirred at room temperature overnight. Zinc acetate in the mixture was filtered off and the filtrate was concentrated and purified by silica gel chromatography (ethyl acetate).

Yield: 307.1 mg(65%)

$^1$H-NMR(CDCl$_3$) 1.63(s, 9H), 7.26–7.31(m, 1H), 7.76–7.83(m, 1H), 7.93(s, 1H), 8.62–8.65(m, 1H), 9.20–9.24(m, 1H)

Example 10

Production of α-(2-thienyl)-N-t-butylnitrone

To a suspension of thiophene-2-carbaldehyde (296.7 mg, 2.65 mmol), 1,1-dimethylnitroethane (542.9 mg, 5.27 mmol) and zinc (516.3 mg, 7.90 mmol) in ethanol (3.0 ml) was added acetic acid (946.6 mg, 15.8 mmol) dropwise at 5° C. while stirring. The mixture was stirred at room temperature for one day. Zinc acetate in the mixture was filtered off and the filtrate was concentrated and purified by silica gel chromatography (hexane/ethyl acetate=1/2).

Yield: 373.9 mg(77%)

$^1$H-NMR(CDCl$_3$) 1.61(s, 9H), 7.14–7.17(m, 1H), 7.43–7.47(m, 2H), 8.04(s, 1H)

Example 11

Production of α-($^2$-pyrrolyl)-N-t-butylnitrone

To a suspension of pyrrole-2-carbaldehyde (277.8 mg, 2.92 mmol), 1,1-dimethylnitroethane (601.1 mg, 5.83 mmol) and zinc (572.5 mg, 8.76 mmol) in ethanol (4.0 ml) was added acetic acid (1.05 g, 17.5 mmol) dropwise at 5° C. while stirring. The mixture was stirred at room temperature for one day. Zinc acetate in the mixture was filtered off and the filtrate was concentrated and purified by silica gel chromatography (hexane/ethyl acetate=1/1–2/3).

Yield: 421.6 mg(87%)

$^1$H-NMR(CDCl$_3$) 1.57(s, 9H), 6.30–6.33(m, 1H), 6.50–6.53(m, 1H), 6.93–6.94(m, 1H), 7.52(s, 1H), 12.01 (brs, 1H)

Example 12

Production of α-($^4$-pyrazolyl)-N-t-butylnitrone

To a suspension of 1,1-dimethylnitroethane (546.0 mg, 5.29 mmol) and zinc (515.5 mg, 7.89 mmol) in ethanol (3.0 ml) was added acetic acid (950.0 mg, 15.8 mmol) dropwise at 5° C. while stirring. The mixture was stirred at room temperature for 45 minutes. After cooling the mixture to 5° C. again, pyrazole-4-carbaldehyde (255.4 mg, 2.66 mmol) was added dropwise to the mixture while stirring and stirred at room temperature overnight. Zinc acetate in the mixture was filtered off and the filtrate was concentrated and purified by silica gel chromatography (chloroform/methanol=10/1).

Yield: 226.3 mg(51%)

$^1$H-NMR(CDCl$_3$) 1.60(s, 9H), 6.56(d, 1H, J=2.0 Hz), 7.64(d, 1H, J=2.0 Hz), 7.71(s, 1H), 8.43(brs, 1H)

Example 13

Production of α-(2-phenylethenyl)-N-t-butylnitrone

To a suspension of cinnamaldehyde (769.8 mg, 5.82 mmol), 1,1-dimethylnitroethane (1.20 g, 11.6 mmol) and zinc (1.14 g, 17.4 mmol) in ethanol (30 ml) was added acetic acid (2.10 g, 35.0 mmol) dropwise at 5° C. while stirring. The mixture was stirred at room temperature for 3 hours and let stand for 6 days. After cooling the mixture to 5° C., zinc acetate was filtered off and the filtrate was concentrated and purified by silica gel chromatography (hexane/ethyl acetate= 1/1–0/1).

Yield: 541.4 mg(46%)

$^1$H-NMR(CDCl$_3$) 1.56(s, 9H), 7.01(d, 1H, J=15.8 Hz), 7.28–7.38(m, 3H), 7.43–7.58(m, 4H)

Example 14

Production of N-(2,4-difluorophenylmethyl)-N-[dimethyl(methoxymethyl) methyl]amine 1) Synthesis of 2-t-butoxycarbonylamino-2-methyl-1-propanol A solution of 2-amino-2-methyl-1-propanol (921.2 mg, 10.33 mmol) in dichloromethane (5 ml) was cooled to 0° C. To the mixture was added a solution of di-t-butyl carbonate (Boc$_2$O)(2.1045 g, 9.64 mmol) in dichloromethane (5 ml) dropwise for 30 minutes. After addition, the mixture was warmed to room temperature and stirred for 5 hours. The mixture was added to sat. NaHCO$_3$ aqueous solution and extracted three times with ethyl acetate. The extract was dried over MgSO$_4$ and concentrated to give the crude title compound (1.7204 g: 88%).

$^1$H-NMR(CDCl$_3$) 4.63(br, s, 1H), 4.0(br, s, 1H), 3.59(d, J=6.3 Hz, 2H), 1.43(s, 9H), 1.25(s, 6H)

2) Synthesis of 2-t-butoxycarbonylamino-2-methyl-1-methoxypropane

A suspension of 60% NaH (635.7 mg, 15.89 mmol) in THF (10 ml) was cooled to 0° C. To the mixture was added a solution of 2-t-butoxycarbonylamino-2-methyl-1-propanol (1.5398 g, 8.14 mmol) in THF (5 ml) dropwise, and stirred for 1.5 hours. To the mixture was added a solution of methyl iodide (0.50 ml, 8.03 mmol) in THF (5 ml) dropwise at 0° C., and stirred for 2.5 hours. The reaction mixture was added to water and extracted three times with ethyl acetate. The extract was dried over MgSO$_4$, concentrated and purified by silica gel chromatography (hexane/ethyl acetate=5/1–0/1) to give the title compound (422 mg; 26%).

$^1$H-NMR(CDCl$_3$) 4.75(br, s, 1H), 3.37(s, 3H), 3.31(s, 2H), 1.43(s, 9H), 1.29(s, 6H)

3) Synthesis of 2-amino-2-methyl-1-methoxypropane hydrochloride

To a solution of 2-t-butoxycarbonylamino-2-methyl-1-methoxypropane (422 mg, 2.08 mmol) in ether (5 ml) was added 4N HCl/dioxane and stirred for 22 hours. The solvent was removed in vacuo to give the crude title compound (342.1 mg).

$^1$H-NMR(CDCl$_3$) 8.32(brs, 3H), 3.42(s, 5H), 1.46 (s, 6H)

4) N-(2,4-difluorobenzylidene)-N-[dimethyl (methoxymethyl)methyl]amine

To a solution of the obtained 2-amino-2-methyl-1-methoxypropane hydrochloride (422 mg, 2.08 mmol) in toluene (7 ml) was added 2,4-difluorobenzaldehyde (310 mg, 2.18 mmol) and stirred under reflux using a Dean-Stark trap to remove water for 1 hour. Then triethylamine (1.0 ml) was added to the mixture and stirred for 6 hours. The precipitated hydrochloride was filtered off and the solvent was evaporated to give the crude title compound (547.5 mg).

$^1$H-NMR(CDCl$_3$) 8.51(s, 1H), 8.02(td, J=8.6, 6.6 Hz, 1H), 6.93–6.76(m, 2H), 3.39(s, 2H), 3.36(s, 3H), 1.27(s, 6H)

5) N-(2,4-difluorophenylmethyl)-N-[dimethyl (methoxymethyl)methyl]amine

A solution of the obtained N-(2,4-difluorobenzylidene)-N-[dimethyl(methoxymethyl)methyl]amine in methanol (7 ml) was cooled to 0° C. in ice-water bath. To the solution was added NaBH$_4$ (117.1 mg, 3.09 mmol). The mixture was gradually warmed to room temperature and stirred for 14 hours. The mixture was added to sat. NaHCO$_3$ aqueous solution and water was added to dissolve the precipitated white solid. The mixture was then extracted three times with ethyl acetate and dried over MgSO$_4$. The mixture was concentrated and purified by silica gel chromatography (hexane/ethyl acetate/triethylamine=50/25/1) to give N-(2, 4-difluorophenylmethyl) -N-[dimethyl(methoxymethyl) methyl]amine (378.8 mg; 95% in 3 steps).

$^1$H-NMR(CDCl$_3$) 7.36(td, J=8.6, 6.6 Hz, 1H), 6.87–6.72 (m, 2H), 4.72(s, 1H), 3.69(s, 2H), 3.36(s, 3H), 3.24(s, 2H), 1.13(s, 6H)

Example 15

Production of α-(2,4-difluorophenyl)-N-[dimethyl (methoxymethyl) methyl]nitrone

A solution of N-(2,4-difluorophenylmethyl)-N-[dimethyl (methoxymethyl)methyl]amine obtained in Example 14

(378.8 mg, 1.65 mmol) and Na₂WO₄ 2H₂O (84.3 mg, 0.256 mmol) in methanol (5 ml) was cooled to 0° C. in ice-water bath. To the mixture was added dropwise 31% $H_2O_2$ aqueous solution (439.3 mg, 4.00 mmol). After addition the mixture was gradually warmed to room temperature and stirred for 15 hours. The mixture was added to sat. NaCl aqueous solution and extracted three times with ethyl acetate and dried over MgSO₄. The mixture was concentrated and purified by silica gel chromatography (toluene/ethyl acetate=5/1) to give the title compound (204.8 mg; 51%).

$^1$H-NMR(CDCl₃) 9.43(td, J=8.7, 6.9 Hz, 1H), 7.77(s, 1H), 6.97–6.89(m, 1H), 6.84(ddd, J=11.2, 8.7, 2.6 Hz, 1H), 3.65(s, 2H), 3.36(s, 3H), 1.58(s, 6H)

Example 16

Production of α-(2,4-difluorophenyl)-N-[dimethyl (methoxymethoxymethyl)methyl]nitrone 1) 2-methyl-2-nitro-1-(methoxymethoxy)propane To a solution of 2-methyl-2-nitro-1-propanol (366.8 mg, 3.08 mmol) and LiBr (60.8 mg, 0.700 mmol) in dimethoxymethane (5 ml) was added p-toluenesulfonic acid hydrate (56.3 mg, 0.296 mmol) and stirred for 24 hours. The mixture was added to water and extracted three times with ethyl acetate and dried over MgSO₄. The mixture was concentrated and purified by silica gel chromatography (hexane/ether=4/1) to give the title compound (382.7 mg; 76%).

$^1$H-NMR(CDCl₃) 4.61(s, 2H), 3.81(s, 2H), 3.34(s, 3H), 1.61(s, 6H)

2) α-(2,4-difluropheyl)-N-[dimethyl (methoxymethoxymethyl)methyl]nitrone

A suspension of 2,4-difluorobenzaldehyde (293.3 mg, 2.06 mmol), 2-methyl-2-nitro-1-(methoxymethoxy)propane (382.7 mg, 2.35 mmol) and zinc (266 mg, 4.07 mmol) in ethanol (5 ml) was cooled to 0° C. in ice-water bath. Acetic acid (0.46 ml, 8.0 mmol) was added dropwise to the mixture. The mixture was gradually warmed to room temperature and stirred for 19 hours. The mixture was filtered through Celite® bed and the filtrate was concentrated and purified by silica gel chromatography (hexane/ethyl acetate=4/1) to give the title compound (361.9 mg; 56%).

$^1$H-NMR(CDCl₃) 9.43(td, J=8.7, 6.9 Hz, 1H), 7.79(s, 1H), 6.96–6.89 (m, 1H), 6.84(ddd, J=11.2, 8.7, 2.6 Hz, 1H), 4.61(s, 2H), 3.81(s, 21), 3.33(s, 3H), 1.61(s, 6H)

Example 17

Production of α-(2,4-difluorophenyl)-N-[dimethyl (acetoxymethyl) methyl]nitrone 1) 2-methyl-2-nitro-1-acetoxypropane Acetic anhydride (0.34 ml, 3.60 mmol) was added to a solution of 2-methyl-2-nitro-1-propanol (375.4 mg, 3.15 mmol) and triethylamine (0.80 ml, 5.74 mmol) in dichloromethane (5 ml) and stirred for 2.5 hours. The mixture was concentrated and purified by silica gel chromatography (hexane/ether=3/1) to give the title compound (467.8 mg; 92%).

$^1$H-NMR(CDCl₃) 4.40(s, 2H), 2.08(s, 3H), 1.62(s, 6H)

2) α-(2,4-difluorophenyl)-N-[dimethyl(acetoxymethyl) methyl]nitrone

A suspension of 2,4-difluorobenzaldehyde (428.2 mg, 3.01 mmol), 2-methyl-2-nitro-1-acetoxypropane (467.8 mg, 2.90 mmol) and zinc (321.7 mg, 4.92 mmol) in ethanol (5 ml) was cooled to 0° C. in ice-water bath. Acetic acid (0.57 ml, 9.9 mmol) was added dropwise to the mixture and was warmed to room temperature and stirred for 16 hours. The mixture was filtered through Celite® bed and the filtrate was concentrated and purified by silica gel chromatography (hexane/ethyl acetate=2/1) to give the title compound (380.8 mg; 48%).

$^1$H-NMR(CDCl₃) 9.41(td, J=8.7, 6.9 Hz, 1H), 7.75(s, 1H), 7.00–6.91(m, 1H), 6.86(ddd, J=11.2, 8.7, 2.6 Hz, 1H), 4.42(s, 2H), 2.05(s, 3H), 1.62(s, 6H)

Example 18

Production of N-(2,4-difluorophenylmethyl)-N-t-butylnitrone

1) N-(2,4-difluorobenzylidene)-t-butylamine

To a solution of 2,4-difluorobenzaldehyde (431.6 mg, 3.04 mmol) in toluene (5 ml) was added t-butylamine (0.63 ml, 6.00 mmol) and stirred under reflux using a Dean-Stark trap to remove water for 1 hour. Then t-butylamine (0.63 ml, 6.00 mmol) was added to the mixture and stirred for 5 hours. The solvent was evaporated to give the title compound.

$^1$H-NMR(CDCl₃) 8.49(s, 1H), 8.02(td, J=8.6, 6.6 Hz, 1H), 6.93–6.76 (m, 2H), 1.29(s, 9H)

2) N-(2,4-difluorophenylmethyl)-N-t-butylamine

A solution of the obtained N-(2,4-difluorobenzylidene)-t-butylamine in methanol (5 ml) was cooled to 0° C. in ice-water bath. To the solution was added NaBH₄ (138.3 mg, 3.65 mmol). The mixture was gradually warmed to room temperature and stirred for 2.5 hours. The mixture was added to sat. NaHCO₃ aqueous solution, extracted three times with ethyl acetate and dried over MgSO₄. The mixture was concentrated and purified by silica gel chromatography (hexane/ethyl acetate/triethylamine=100/5/1) to give the title compound (504.2 mg; 83%, 2 steps).

$^1$H-NMR(CDCl₃) 7.41–7.31(m, 1H), 6.86–6.73(m, 2H), 3.73(s, 2H), 1.42(br, 1H), 1.17(s, 9H)

Example 19

Production of α-(3,4-difluorophenyl)-N-t-butylnitrone

A suspension of 3,4-difluorobenzaldehyde (289.1 mg, 2.03 mmol), 2-methyl-2-nitropropane (413.5 mg, 4.01 mmol) and zinc (399 mg, 6.10 mmol) in ethanol (5 ml) was cooled to 0° C. in ice-water bath. Acetic acid (0.69 ml, 12.0 mmol) was added dropwise to the mixture. The mixture was gradually warmed to room temperature, stirred for 2.5 hours and let stand overnight. The mixture was filtered through Celite® bed and the filtrate was concentrated and purified by silica gel chromatography (hexane/ethyl acetate=10/1) to give the title compound (394.2 mg; 91%).

$^1$H-NMR(CDCl₃) 8.58(ddd, J=12.5, 8.2, 2.0 Hz, 1H), 7.78–7.72(m, 1H), 7.52(s, 1H), 7.18(dt, J=10.1, 8.4 Hz, 1H), 1.61(s, 9H)

Example 20

Production of α-(2,5-difluorophenyl)-N-t-butylnitrone

A suspension of 2,5-difluorobenzaldehyde (291.5 mg, 2.05 mmol), 2-methyl-2-nitropropane (427.3 mg, 4.14 mmol) and zinc (407.3 mg, 6.23 mmol) in ethanol (5 ml) was cooled to 0° C. in ice-water bath. Acetic acid (0.69 ml, 12.0 mmol) was added dropwise to the mixture. The mixture was gradually warmed to room temperature, stirred for 2 hours and let stand overnight. The mixture was filtered through Celite® bed and the filtrate was concentrated and purified by silica gel chromatography (hexane/ethyl acetate=10/1) to give the title compound (393 mg; 90%).

$^1$H-NMR(CDCl₃) 9.16–9.08(m, 1H), 7.84(d, J =1.3 Hz, 1H), 7.07–7.01(m, 2H), 1.62(s, 9H)

Example 21

Production of α-(2,4-difluorophenyl)-N-[dimethyl (hydroxymethyl) methyl]nitrone

1) N-(2,4-difluorophenylmethyl)-N-[dimethyl(t-butyldimethylsiloxymethyl)methyl]amine To a solution of 2,4-difluorobenzaldehyde (1.42 g, 10.0 mmol) in toluene (30 ml) was added 1-t-butyldimethylsiloxy-2-methyl-2-propylamine (2.03 g, 10.0 mmol) and stirred under reflux using a Dean-Stark trap to remove water for 6 hours. The solvent was evaporated and the residue was dissolved in methanol (10 ml). The solution was cooled to 0° C. in ice-water bath and an excess amount of $NaBH_4$ was added. The mixture was gradually warmed to room temperature and stirring was continued until the Schiff base disappeared. The mixture was added to 1N NaOH aqueous solution, extracted with toluene, washed with sat. NaCl aqueous solution and dried over $MgSO_4$. The solvent was evaporated to give the crude title compound (2.92 g; 92% in 2 steps).

$^1$H-NMR($CDCl_3$) 7.40–7.14.(m, 1H), 6.86–6.72 (m, 2H), 3.67 (d, 2H, J=9.0 Hz), 3.42 (s, 2H), 1.91–61 (br, 1H), 1.10 (s, 6H), 0.94 (s, 9H), 0.08 (s, 6H)

2) α-(2,4-difluorophenyl)-N-[dimethyl(t-butyldimethylsiloxymethyl) methyl]nitrone A solution of N-(2,4-difluorophenylmethyl)-N-[dimethyl (methoxymethyl)methyl]amine (2.0 g, 6.08 mmol) and $Na_2WO_4$ $2H_2O$ (0.080 g, 0.24 mmol) in methanol (10 ml) was cooled to 0° C. in ice-water bath. To the mixture was added dropwise 31% $H_2O_2$ aqueous solution (2 ml). After addition the mixture was gradually warmed to room temperature and stirred overnight. The mixture was added to sat. NaCl aqueous solution and extracted three times with ethyl acetate and dried over $MgSO_4$. The mixture was concentrated and purified by silica gel chromatography (hexane/ethyl acetate=5/1) to give the title compound (1.53 g; 73%).

$^1$H-NMR($CDCl_3$) 9.41 (td, 1H, J=8.7, 6.9 Hz), 7.77 (s, 1H), 6.96–6.89 (m, 1H), 6.83 (ddd, 1H, J=11.2, 8.7, 2.6 Hz), 3.79 (s, 2H), 1.56 (s, 6H), 0.83 (s, 9H), 0.00 (s, 6H)

3) α-(2,4-difluorophenyl)-N-[dimethyl(hydroxymethyl) methyl]nitrone

A solution of α-(2,4-difluorophenyl)-N-[dimethyl(t-butyldimethylsiloxymethyl) methyl]nitrone (688.3 mg, 2.00 mmol) in THF (20 ml) was cooled to 0° C. in ice-water bath. To the mixture was added carefully hydrogen fluoride-pyridine (1 ml). The mixture was gradually warmed to room temperature and stirred for 7 hours. The mixture was added to sat. $NaHCO_3$ aqueous solution and extracted three times with ethyl acetate and dried over $MgSO_4$. The solvent was evaporated and the white crystals were washed with hexane to give the title compound (317.3 mg; 69%).

$^1$H-NMR($CDCl_3$) 9.35 (td, 1H, J=8.7, 6.9 Hz), 7.73 (s, 1H), 7.01–6.92 (m, 1H), 6.87 (ddd, 1H, J=11.2, 8.7, 2.6 Hz), 3.94 (t, 1H, J=5.9 Hz), 3.80 (d, 2H, J=5.9 Hz), 1.61 (s, 6H)

Example 22

Production of α-(2,4-difluorophenyl)-N-[dimethyl (benzyloxymethyl) methyl]nitrone 1) 2-methyl-2-nitro-1-benzyloxypropane To a suspension of 2-methyl-2-nitro-1-propanol (2.3975 g, 20.13 mmol) and $Ag_2O$ (4.6385 g, 20.02 mmol) in DMF (25 ml) was added benzyl bromide (2.65ml, 22.28 mmol) and stirred for 48 hours. The mixture was filtered and the filtrate was added to 5% $KHSO_4$ aqueous solution, extracted three times with ethyl acetate/hexane=1/1 and dried over $MgSO_4$. The mixture was concentrated and purified by silica gel chromatography (toluene) to give the title compound (639.4 mg; 15%).

$^1$H-NMR($CDCl_3$) 7.38–7.25 (m, 51), 4.54 (s, 2H), 3.72 (s, 2H), 1.59 (s, 6H)

2) α-(2,4-difluorophenyl)-N-[dimethyl(benzyloxymethyl) methyl]nitrone

A suspension of 2,4-difluorobenzaldehyde (443.7 mg, 3.12 mmol), 2-methyl-2-nitro-1-benzyloxypropane (639.4 mg, 3.06 mmol) and zinc (326.4 mg, 4.99 mmol) in ethanol (6 ml) was cooled to 0° C. in ice-water bath. Acetic acid (0.57 ml, 9.9 mmol) was added dropwise to the mixture. The mixture was gradually warmed to room temperature and stirred for 7 hours. The mixture was filtered through Celite® bed and the filtrate was concentrated and purified by silica gel chromatography (hexane/ethyl acetate=10/1–4/1) to give the title compound (468.8 mg; 48%).

$^1$H-NMR($CDCl_3$) 9.43 (td, 1H, J=8.9, 6.9 Hz), 7.82 (s, 1H), 7.38–7.25 (m, 5H), 6.99–6.80 (m, 2H), 4.54 (s, 2H), 3.73 (s, 21), 1.59 (s, 6H)

Example 23

Production of α-(2,4-difluorophenyl)-N-[dimethyl (3,3-ethylenedioxy-1-propyl)methyl]nitrone A suspension of 2,4-difluorobenzaldehyde (290.6 mg, 2.04 mmol), 2-(3-methyl-3-nitrobutyl)-1,3-dioxolane (776.8 mg, 4.11 mmol) and zinc (402.7 mg, 6.16 mmol) in ethanol (5 ml) was cooled to 0° C. in ice-water bath. Acetic acid (0.69 ml, 12.0 mmol) was added dropwise to the mixture. The mixture was gradually warmed to room temperature and stirred for 10 hours and let stand overnight. The mixture was filtered through Celite® bed and the filtrate was concentrated and purified by silica gel chromatography (hexane/ethyl acetate=4/1–1/1) to give the title compound (419.4 mg; 69%).

$^1$H-NMR($CDCl_3$) 9.41 (td, 1H, J=8.6, 6.9 Hz), 7.72 (s, 1H), 6.96–6.88 (m, 1H), 6.84 (ddd, 1H, J=11.2, 8.6, 2.6 Hz), 4.86 (t, 1H, d=4.6 Hz), 3.99–3.81 (m, 4H), 2.05–1.98 (m, 2H), 1.65–1.58 (m, 2H), 1.59 (s, 6H)

Example 24

Production of α-(2-fluoro-4-methoxyphenyl)-N-t-butylnitrone 1) methyl 2,4-difluorobenzoate A solution of 2,4-difluorobenzoic acid (1.5808 g, 10.00 mmol) in methanol (15 ml) was cooled to 0° C. in ice-water bath. To the mixture was added dropwise a solution of thionyl chloride (1.46 ml, 20.02 mmol) in methanol (10 ml). The mixture was gradually warmed to room temperature and stirred for 24 hours. The mixture was added to sat. $NaHCO_3$ aqueous solution, extracted three times with ether and dried over $MgSO_4$. The mixture was concentrated and purified by silica gel chromatography (hexane/ether=5/1) to give the title compound (1.6743 g; 97%).

$^1$H-NMR($CDCl_3$) 7.99 (td, 1H, J=8.2, 6.6 Hz), 6.98–6.84 (m, 2H), 3.93 (s, 3H)

2) methyl 2-fluoro-4-methoxybenzoate and methyl 4-fluoro-2-methoxybenzoate

A solution of methyl 2,4-difluorobenzoate (1.5249 g, 8.76 mmol) in methanol (10 ml) was cooled to 0° C. in ice-water bath. To the mixture was added 28% solution of sodium methoxide in methanol (1.9860 g, 10.29 mmol). The mixture was gradually warmed to room temperature and stirred for 24 hours. The mixture was added to water, extracted three times with ethyl acetate and dried over $MgSO_4$. The mixture was concentrated and purified by silica gel chromatography (hexane/ether=10/1) to give the title compound:methyl 2-fluoro-4-methoxybenzoate (618.2 mg; 38%) and methyl 4-fluoro-2-methoxybenzoate (442.2 mg; 27%).

Methyl 2-fluoro-4-methoxybenzoate: $^1$H-NMR($CDCl_3$) 7.90 (t, 1H, J=8.7 Hz), 6.72 (ddd, 1H, J=8.7, 2.3, 0.7 Hz), 6.64 (dd, 1H, J=12.5, 2.3 Hz), 3.90 (s, 3H), 3.85 (s, 3H)

Methyl 4-fluoro-2-methoxybenzoate: $^1$H-NMR($CDCl_3$) 7.86 (dd, 1H, J=9.1, 6.8 Hz), 6.71–6.64 (m, 2H), 3.90 (s, 3H), 3.88 (s, 3H)

3) 2-fluoro-4-methoxybenzylalcohol

To a suspension of LiAlH$_4$ (71.6 mg, 1.89 mmol) in THF (3 ml) was added dropwise a solution of methyl 2-fluoro-4-methoxybenzoate (273.3 mg, 1.48 mmol) in THF (3 ml). The mixture was stirred for 0.5 hours. To the mixture was added dropwise aqueous THF followed by water. The mixture was extracted three times with ethyl acetate and dried over MgSO$_4$. The solvent was evaporated to give the crude title compound (240.4 mg; >99%).

$^1$H-NMR(CDCl$_3$) 7.29 (t, 1H, J=8.6 Hz), 6.69 (dd, 1H, J=8.6, 2.6 Hz), 6.63 (dd, 1H, J=11.7, 2.6 Hz), 4.68 (d, 2H, J=5.0 Hz), 3.80 (s, 3H), 1.65 (t, 1H, J=5.0 Hz)

4) 2-fluoro-4-methoxybenzaldehyde

Triethylamine (0.92 ml, 6.60 mmol) was added to a solution of 2-fluoro-4-methoxybenzylalcohol (346.9 mg, 2.22 mmol) in DMSO (8 ml). Pyridine sulfur trioxide (1.0501 g, 6.60 mmol) was added portionwise to the mixture checking raise of the temperature. The mixture was stirred for 0.5 hours. The mixture was added to 5% KHSO$_4$ aqueous solution, extracted three times with ethyl acetate and dried over MgSO$_4$. The mixture was concentrated and purified by silica gel chromatography (hexane/ether=5/1) to give the title compound (301 mg; 88%).

$^1$H-NMR(CDCl$_3$) 10.21 (s, 1H), 7.83 (t, 1H, J =8.3 Hz), 6.79 (ddd, 1H, J=8.3, 2.3, 0.7 Hz), 6.65 (dd, 1H, J=12.2, 2.3 Hz), 3.88 (s, 3H)

5) α-(2-fluoro-4-methoxyphenyl)-N-t-butylnitrone

The title compound (373.9 mg; 85%) was prepared by the same method as that described in Example 1, using 2-fluoro-4-methoxybenzaldehyde (301 mg, 1.95 mmol).

$^1$H-NMR(CDCl$_3$) 9.34 (t, 1H, J=9.1 Hz), 7.75 (s, 1H), 6.74 (dd, 1H, J=9.1, 2.6 Hz), 6.64 (dd, 1H, J=13.0, 2.6 Hz), 3.84 (s, 3H), 1.61 (s, 9H)

Example 25

Production of α-(4-fluoro-2-methoxyphenyl)-N-t-butylnitrone 1) 4-floro-2-methoxybenzylalcohol To a suspension of LiAlH$_4$ (94.6 mg, 2.49 mmol) in THF (3 ml) was added dropwise a solution of methyl 4-fluoro-2-methoxybenzoate obtained in Example 23–2) (273.3 mg, 1.48 mmol) in THF (3 ml). The mixture was stirred for 1 hour. To the mixture was added dropwise aqueous THF followed by water. The mixture was extracted three times with ethyl acetate and dried over MgSO$_4$. The solvent was evaporated to give the crude title compound (310.8 mg; 83%).

$^1$H-NMR(CDCl$_3$) 7.23 (dd, 1H, J=8.6, 6.6 Hz), 6.68–6.59 (m, 2H), 4.64 (d, 2H, J=6.3 Hz), 3.86 (s, 3H), 2.13 (t, 1H, J=6.3 Hz)

2) 4-fluoro-2-methoxybenzal dehyde

Triethylamine (0.84 ml, 6.03 mmol) was added to a solution of 4-fluoro-2-methoxybenzylalcohol (310.8 mg, 1.99 mmol) in DMSO (7 ml). Pyridine sulfur trioxide (938.6 mg, 5.90 mmol) was added portionwise to the mixture checking raise of the temperature. The mixture was stirred for 1 hour. The mixture was added to 5% KHSO$_4$ aqueous solution, extracted three times with ethyl acetate and dried over MgSO$_4$. The mixture was concentrated and purified by silica gel chromatography (hexane/ether=5/1) to give the title compound (293.3 mg; 96%).

$^1$H-NMR(CDCl$_3$) 10.36 (d, 1H, J=0.8 Hz), 7.86 (dd, 1H, J=8.6, 6.9 Hz), 6.73 (tdd, 1H, J=8.6, 2.3, 0.8 Hz), 6.69 (dd, 1H, J=10.6, 2.3 Hz), 3.93 (s, 3H)

3) α-(4-fluoro-2-methoxyphenyl)-N-t-butylnitrone

The title compound (405.7 mg; 95%) was prepared by the same method as that described in Example 1, using 4-fluoro-2-methoxybenzaldehyde (293.3 mg, 1.90 mmol).

$^1$H-NMR(CDCl$_3$) 9.44 (dd, 1H, J=8.9, 7.3 Hz), 7.95 (s, 1H), 6.71 (td, 1H, J=8.9, 2.3 Hz), 6.60 (dd, 1H, J=10.8, 2.3 Hz), 3.87 (m , 3H), 1.54 (s, 9H)

Example 26

Production of α-(4-trifluoromethylphenyl)-N-t-butylnitrone

The title compound (445.2 mg; 92%) was prepared by the same method as that described in Example 1, using 4-trifluoromethylbenzaldehyde (343.7 mg, 1.97 mmol).

$^1$H-NMR(CDCl$_3$) 8.39 (d, 2H, J=8.4 Hz), 7.66 (d, 2H, J=8.4 Hz), 7.62 (s, 1H), 1.63 (s, 9H)

Example 27

Production of α-(4-bromophenyl)-N-t-butylnitrone

The title compound (492.1 mg; 96%) was prepared by the same method as that described in Example 1, using 4-bromobenzaldehyde (372.2 mg, 2.01 mmol).

$^1$H-NMR(CDCl$_3$) 8.17 (dd, 2H, J=6.8, 1.7 Hz), 7.54 (dd, 211, J=6.8, 2.0 Hz), 7.51 (s, 1H), 1.61 (s, 9H)

Example 28

Production of α-(4-methoxyphenyl)-N-t-butylnitrone

The title compound (412.4 mg; 98%) was prepared by the same method as that described in Example 1, using p-anisaldehyde (274.9 mg, 2.02 mmol).

$^1$H-NMR(CDCl$_3$) 8.29 (d, 2H, J=9.1 Hz), 7.47 (s, 1H), 6.93 (d, 2H, J=9.1 Hz) ,3.85 (s, 3H), 1.61(s, 9H)

Example 29

Production of α-(4-trifluoromethoxyphenyl)-N-t-butylnitrone

The title compound (353.9 mg; 88%) was prepared by the same method as that described in Example 1, using 4-(trifluoromethoxy)-benzaldehyde (293.2 mg, 1.54 mmol).

$^1$H-NMR(CDCl$_3$) 8.36 (d, 2H, J=9.2 Hz), 7.56 (s, 1H), 7.25 (d, 2H, J=9.2 Hz), 1.62(s, 9H)

Example 30

Production of α-(4-cyanophenyl)-N-t-butylnitrone

To a solution of 4-cyanobenzaldehyde (392.9 mg, 3.00 mmol) and t-butylamine (227.3 mg, 3.10 mmol) in 1,2-dichloroethane (12 ml) was added sodium triacetoxyborohydride (0.8567 g, 4.04 mmol) and stirred for 3 hours. Acetic acid (0.17 ml, 2.95 mmol) was added to the mixture and stirred for 2.5 hours. The mixture was added to sat. NaHCO$_3$ aqueous solution, extracted three times with ethyl acetate and dried over MgSO$_4$. The solvent was evaporated to give the crude title compound (595.3 mg).

$^1$H-NMR(CDCl$_3$) 7.60 (d, 2H, J=8.4 Hz), 7.47 (d, 21, J=8.4 Hz), 3.79 (s, 2H), 1.17 (s, 9H)

Example 31

Production of α(4-cyanophenylmethyl)-N-t-butylamine

A solution of N-(4-cyanophenylmethyl)-N-t-butylamine obtained in Example 30 (595.3 mg) and Na$_2$WO$_4$ 2H$_2$O (105.7 mg, 0.320 mmol) in methanol (5 ml) was cooled to 0° C. in ice-water bath. To the mixture was added dropwise 31% H$_2$O$_2$ aqueous solution (786.2 mg, 7.17 mmol). After addition the mixture was gradually warmed to room temperature and stirred for 14 hours. The mixture was added to water and extracted three times with ethyl acetate and dried over MgSO$_4$. The mixture was concentrated and purified by silica gel chromatography (hexane/ethyl acetate=2/1–1–1) to give the title compound (272.3 mg; 45%, 2 steps).

$^1$H-NMR(CDCl$_3$) 8.37 (d, 2H, J=8.6 Hz), 7.68 (d, 2H, J=8.6 Hz), 7.62 (s, 1H), 1.62 (s, 9H)

Example 32

Production of α-(2-chloro-4-fluorophenyl)-N-t-butylnitrone

The title compound (387.8 mg; 84%) was prepared by the same method as that described in Example 1, using 2-chloro-4-fluorobenzaldehyde (316.6 mg, 2.00 mmol).

$^1$H-NMR(CDCl$_3$) 9.48 (dd, 1H, J=8.9, 6.6 Hz), 8.02 (s, 1H), 7.17 (dd, 1H, J=8.3, 2.6 Hz), 7.10–7.01 (m, 1H), 1.63 (s, 9H)

Example 33

Production of α-(4-fluoro-2-trifluoromethylphenyl)-N-t-butylnitrone

The title compound (310.8 mg; 79%) was prepared by the same method as that described in Example 1, using 4-fluoro-2-trifluoromethylbenzaldehyde (286.2 mg, 1.49 mmol).

$^1$H-NMR(CDCl$_3$) 9.57 (dd, 1H, J=8.9, 5.8 Hz), 7.88 (s, 1H), 7.42 (dd, 1H, J=8.9, 3.0 Hz), 7.35–7.26 (m, 1H), 1.61 (s, 91)

Example 34

Production of α-(2-fluoro-4-trifluoromethylphenyl)-N-t-butylnitrone

The title compound (347.2 mg; 87%) was prepared by the same method as that described in Example 1, using 2-fluoro-4-trifluoromethylbenzaldehyde (291.3 mg, 1.52 mmol).

$^1$H-NMR(CDCl$_3$) 9.46 (t, 1H, J=7.6 Hz), 7.89 (s, 1H), 7.48 (d, 1H, J=7.6 Hz), 7.34 (d, 1H, J=10.9 Hz), 1.63 (s, 9H)

The structures of the compounds obtained in Example 1 to 34 are as follows:

Example 1

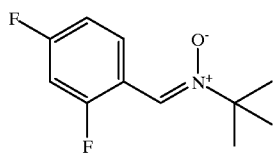

Example 2

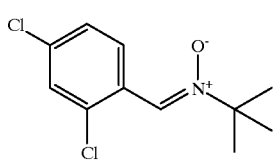

Example 3

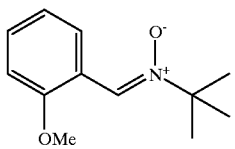

Example 4

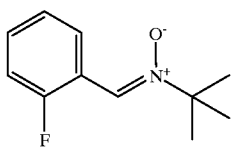

Example 5

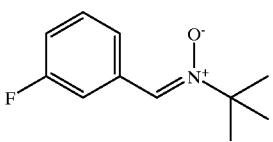

Example 6

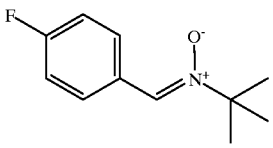

Example 7

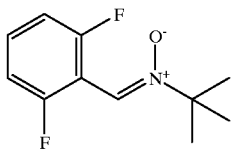

Example 8

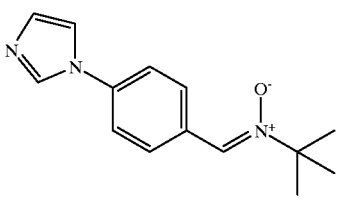

Example 9

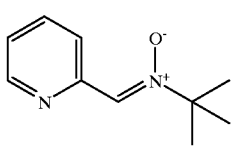

Example 10

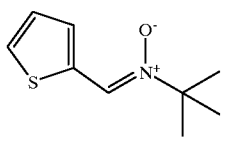

Example 11

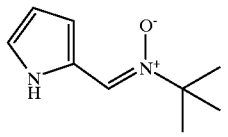

-continued
Example 12
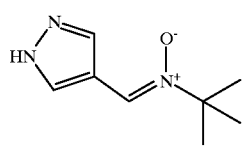
Example 13
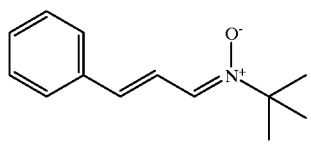
Example 14
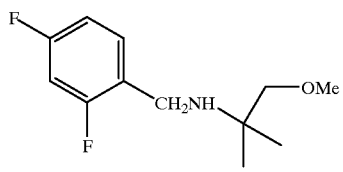
Example 15
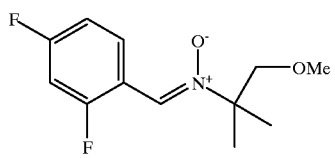
Example 16
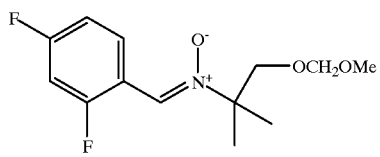
Example 17
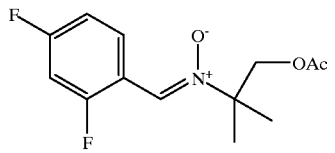
Example 18
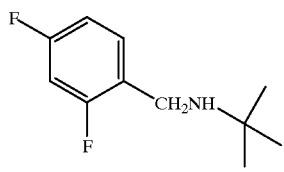
Example 19
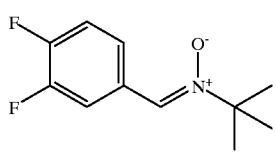
Example 20
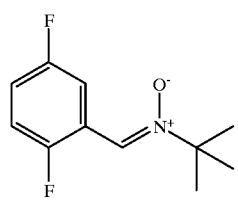
-continued
Example 21
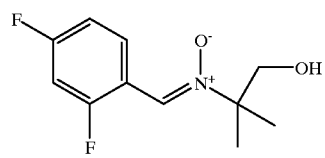
Example 22
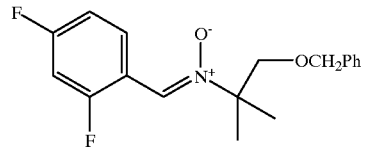
Example 23
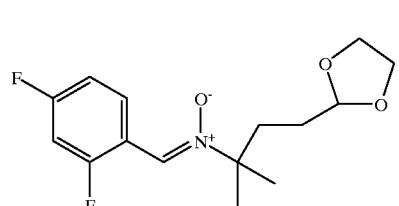
Example 24
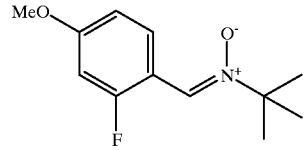
Example 25
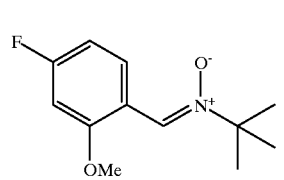
Example 26
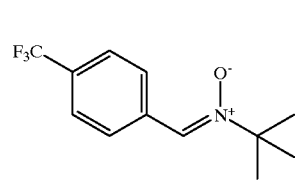
Example 27
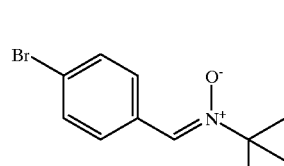
Example 28
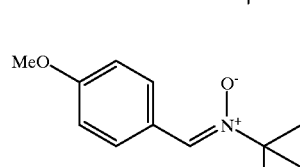
Example 29
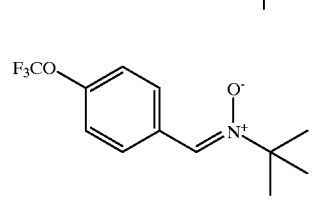

-continued

Example 30
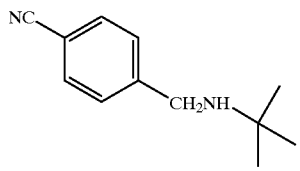

Example 31
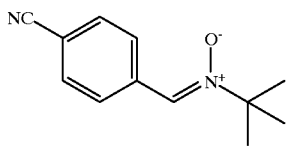

Example 32
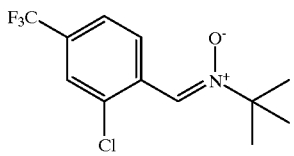

Example 33
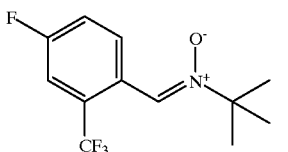

Example 34
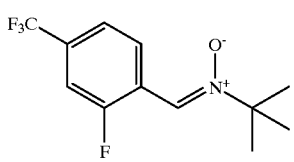

Retinal outer nuclear cells have been known to be degenerated by the constant white light exposure to albino rats (L. M. Rapp, et al., New York: Plenum, 135 (1980)). Effectiveness of the compounds of figures 1 or 2 or pharmaceutical acceptable salts thereof can be evaluated by their protective action against constant light exposure-induced retinal degeneration in rats. The present invention is embodied by the following experiment.

Example 35

Pharmacological Effect Against Constant Light-Induced Retinal Damage

Male Sprague-Dawley rats (8 weeks old, Charles River Japan Inc.) were purchased and maintained in cyclic light/dark environment (8:00–20:00/light term) for one week, and then placed within the apparatus for constant light exposure for two days. The constant light exposure apparatus is a covered breeding box of 1020 mm in length, 425 mm in width, 520 mm in height, which is made of acryl boards and of which all inner side are covered with mirrors. Light was continuously irradiated all the day long (24 hours) using white fluorescent lamp attached to the ceiling of the apparatus. The average illuminance level in the apparatus was 174.2 foot candle. After two days in the apparatus, the rats were moved to a darkroom and dark adapted for 1–4 hours. The rats were anesthetized with pentobarbital and placed in a stereotaxic frame. After topical mydriatica was given and electrodes were put on corneal surface, center of the forehead and the lower part of the lobe, the response in active potential of retina to the flash stimulation with fixed energy was determined from the recorded ERG (electroretinogram). The damage of retina was evaluated by the decrease in the amplitude of ERG α-wave which originated from retinal outer nuclear cells (photoreceptors). Test compound was intraperitoneally injected just before placing the rats into the constant light exposure apparatus and at the same time on the next day to investigate its protective effect.

According to the experimental procedure described above, each test compound in the present invention, which was suspended or dissolved in 0.5 % methylcellulose (MC) solution, was intraperitoneally administered twice to four rats in a group at the dose of 50 mg/kg. In the same way, 0.5 % MC solution was intraperitoneally administered to the rats in MC group. The rats maintained in 12 hours cyclic light/dark environment were used for normal control group. The protection by the compound against the retinal damage was represented as % recovery value, and the results was shown in Table 1.

$$\% \text{ recovery} = (a-c) \div (b-c) \times 100$$

a: α-wave amplitude in test compound group
b: α-wave amplitude in normal control group
c: α-wave amplitude in MC group

TABLE 1

| Compounds | % recovery (Means ± S. E. M.) | N |
|---|---|---|
| PBN | 15.4 ± 6.3 | 8 |
| The compound of Example 1 | 105.0 ± 8.0 | 4 |
| The compound of Example 2 | 36.4 ± 5.2 | 4 |
| The compound of Example 10 | 22.2 ± 8.1 | 4 |
| The compound of Example 18 | 24.8 ± 5.3 | 4 |
| The compound of Example 26 | 40.1 ± 7.2 | 4 |
| The compound of Example 27 | 58.0 ± 14.7 | 4 |

Example 36

Metabolism of the Compound of Example 18 into the Compound of Example 1 in Vivo

Male Wistar rats (6 weeks old, Charles River Japan Inc.) were purchased and maintained under the controlled environment with constant temperature and humidity for one week before experiments. The compound of Example 18 was suspended at 10 mg/ml in 0.5% MC solution, and intraperitoneally administered under light ether anesthesia (50 mg/kg, 5 mg/kg, n=3). Total blood was collected from descending aorta under ether anesthesia at 30 min and 6 hours after the administration. The serum was obtained by centrifugation of the blood in separapiddotyubu (enhanced coagulation type of ready-made centrifuge tube containing serum separation agent). The concentrations (pg/ml) in serum of the compounds of Example 18 and Example 1 were determined by reversed phase high performance liquid chromatography. The results were shown in Table 2.

TABLE 2

| | After 30 minutes | After 6 hours |
|---|---|---|
| The concentration of the compound of Example 18 | 13.9 | 2.14 |
| The concentration of the compound of Example 1 | 0.42 | 1.67 |

INDUSTRIAL APPLICABILITY

The present invention can provide a medicament for treating retinal degenerative disorders and a novel compound useful as a medicament for treating degenerative disorders.

What is claimed is:

1. A medicament for treating retinal degenerative disorder comprising a compound represented by the figure (1) or a pharmaceutically acceptable salt thereof:

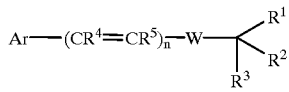
(1)

wherein Ar is optionally substituted phenyl or optionally substituted heteroaryl;
n is 0, 1 or 2;
W is —CH$_2$NH— or —CH=N(O)—;
R$^1$, R$^2$ and R$^3$ are independently optionally substituted alkyl, carboxyl or alkoxycarbonyl; any two groups of R$^1$, R$^2$ and R$^3$ may be taken together with the carbon atom to form optionally substituted cycloalkane; all of R$^1$, R$^2$ and R$^3$ may be taken together with the adjacent carbon atom to form optionally substituted bicycloalkane or optionally substituted tricycloalkane;
R$^4$ and R$^5$ are independently hydrogen atom or optionally substituted alkyl.

2. A medicament for treating retinal degenerative disorder comprising a compound according to claim 1 or a pharmaceutically acceptable salt thereof, wherein the substituent of the substituted phenyl and the substituted heteroaryl is halogen atom, cyano, nitro, alkyl, alkyl substituted by halogen atom(s), alkoxy, alkoxy substituted by halogen atom(s), alkoxycarbonyl, carbamoyl or carbamoyl substituted by alkyl(s); the substituent of the substituted alkyl, the substituted cycloalkane, the substituted bicycloalkane and the substituted tricycloalkane is cycloalkyl, heterocycloalkyl, alkoxy, alkoxyalkoxy, alkanoyloxy or alkanoylamino.

3. A medicament for treating retinal degenerative disorder comprising a compound according to claim 1 or a pharmaceutically acceptable salt thereof, wherein n is 0.

4. A medicament for treating retinal degenerative disorder comprising a compound according to claim 1 or a pharmaceutically acceptable salt thereof, wherein Ar is 2-thienyl or phenyl optionally substituted by 1 to 3 halogen atom(s).

5. A medicament for treating retinal degenerative disorder comprising a compound according to claim 1 or a pharmaceutically acceptable salt thereof, wherein Ar is 2-thienyl, 2,4-difluorophenyl, 4-fluorophenyl, 4-bromophenyl, 2,6-difluorophenyl or 2,4-dichlorophenyl.

6. A medicament for treating retinal degenerative disorder comprising a compound according to claim 1 or a pharmaceutically acceptable salt thereof, wherein R$^1$, R$^2$ and R$^3$ are independently optionally substituted alkyl.

7. A medicament for treating retinal degenerative disorder comprising a compound according to claim 1 or a pharmaceutically acceptable salt thereof, wherein W is —CH=N(O)—.

8. A compound represented by the figure (2) or a pharmaceutically acceptable salt thereof:

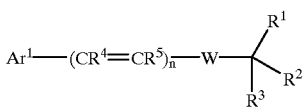
(2)

wherein n, W, R$^1$, R$^2$, R$^3$, R$^4$ and R$^5$ are as defined in claim 1;
Ar$^1$ is optionally substituted 5-membered heteroaryl or a group represented by the figure:

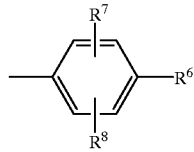

wherein R$^6$ is halogen atom, trifluoromethyl, cyano or nitro;
R$^7$ is hydrogen atom or a substitutent;
R$^8$ is a substituent;
provided that Ar$^1$ is not dichlorophenyl when W is —CH$_2$NH—.

9. A compound according to claim 8 or a pharmaceutically acceptable salt thereof, wherein the substituent of the substituted 5-membered heteroaryl and the substituent represented by R$^7$ and R$^8$ are halogen atom, cyano, nitro, alkyl, alkyl substituted by halogen atom(s), alkoxy, alkoxycarbonyl, carbamoyl or carbamoyl substituted by alkyl(s); the substituent of the substituted alkyl, the substituted cycloalkane, the substituted bicycloalkane and the substituted tricycloalkane is cycloalkyl, heterocycloalkyl, alkoxy, alkoxyalkoxy, alkanoyloxy or alkanoylamino.

10. A compound according to claim 8 or a pharmaceutically acceptable salt thereof, wherein n is 0.

11. A compound according to claim 8 or a pharmaceutically acceptable salt thereof, wherein Ar$^1$ is 2-thienyl or a group represented by the figure:

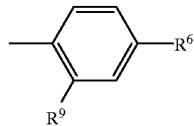

wherein R$^6$ is as defined in claim 8;
R$^9$ is halogen atom, cyano, nitro, alkyl, alkyl substituted by halogen atom(s), alkoxy, alkoxycarbonyl, carbamoyl or carbamoyl substituted by alkyl(s).

12. A compound according to claim 8 or a pharmaceutically acceptable salt thereof, wherein Ar$^1$ is 2-thienyl, 2,4-difluorophenyl, 4-bromophenyl or 2,4-dichlorophenyl.

13. A compound according to claim 8 or a pharmaceutically acceptable salt thereof, wherein R$^1$, R$^2$ and R$^3$ are independently optionally substituted alkyl.

14. A compound according to any one of claim 8 or a pharmaceutically acceptable salt thereof, wherein W is —CH=N(O)—.

* * * * *